(12) United States Patent
Hashino et al.

(10) Patent No.: US 10,786,400 B2
(45) Date of Patent: Sep. 29, 2020

(54) ABSORBENT ARTICLE

(71) Applicant: UNICHARM CORPORATION, Ehime (JP)

(72) Inventors: Akira Hashino, Kagawa (JP); Masashi Uda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 316 days.

(21) Appl. No.: 15/574,183

(22) PCT Filed: Feb. 29, 2016

(86) PCT No.: PCT/JP2016/056116
§ 371 (c)(1),
(2) Date: Nov. 15, 2017

(87) PCT Pub. No.: WO2016/189914
PCT Pub. Date: Dec. 1, 2016

(65) Prior Publication Data
US 2018/0098895 A1    Apr. 12, 2018

(30) Foreign Application Priority Data

May 22, 2015  (JP) ................................. 2015-104888

(51) Int. Cl.
*A61F 13/15*    (2006.01)
*A61F 13/511*   (2006.01)
(Continued)

(52) U.S. Cl.
CPC ...... *A61F 13/51108* (2013.01); *A61F 13/511* (2013.01); *A61F 13/515* (2013.01);
(Continued)

(58) Field of Classification Search
CPC ............. A61F 13/51108; A61F 13/511; A61F 13/5121; A61F 13/515; A61F 13/15804;
(Continued)

(56) References Cited

U.S. PATENT DOCUMENTS 5,449,352 A * 9/1995 Nishino ............ A61F 13/15731
                                                              604/358
6,090,089 A    7/2000 Tsuji et al.
(Continued)

FOREIGN PATENT DOCUMENTS

CN    1294904 A    5/2001
EP    1090615 A1   4/2001
(Continued)

OTHER PUBLICATIONS

International Search Report issued PCT/JP2016/056116, dated May 17, 2016.

*Primary Examiner* — Jacqueline F Stephens
(74) *Attorney, Agent, or Firm* — Hauptman Ham, LLP

(57) ABSTRACT

An absorbent article for minimizing detachment between a top sheet and absorbent body, for stably maintaining an absorption performance, while maintaining a satisfactory feel on a skin of the top sheet. The top sheet has a plurality of raised sections extended in a lengthwise direction at predetermined intervals in a widthwise direction, and a plurality of furrow sections extended in the lengthwise direction between the raised sections. The furrow section has a first recess section including a first bottom section, and a plurality of second recess sections inside the first recess section. The second recess section includes a second bottom section having a highest fiber density of the top sheet. A portion at a second surface of a top section of the raised section is not joined to an absorbent body. The second (Continued)

bottom section of the second recess section of the furrow section is joined to the absorbent body.

13 Claims, 9 Drawing Sheets

(51) Int. Cl.
*A61F 13/512* (2006.01)
*A61F 13/515* (2006.01)
*A61F 13/51* (2006.01)
*A61F 13/513* (2006.01)

(52) U.S. Cl.
CPC .... *A61F 13/5121* (2013.01); *A61F 13/15804* (2013.01); *A61F 2013/15926* (2013.01); *A61F 2013/51026* (2013.01); *A61F 2013/51078* (2013.01); *A61F 2013/51338* (2013.01)

(58) Field of Classification Search
CPC ...... A61F 13/15926; A61F 2013/15926; A61F 2013/51026; A61F 2013/51078; A61F 2013/51338

USPC ............... 604/378, 379, 38, 385.01, 385.101
See application file for complete search history.

(56) References Cited

U.S. PATENT DOCUMENTS

| 6,586,076 B1 | 7/2003 | Mizutani et al. |
| 2005/0148973 A1 | 7/2005 | Tamura et al. |
| 2011/0118691 A1* | 5/2011 | Nishitani ................. B32B 3/30 |
| | | 604/385.101 |

FOREIGN PATENT DOCUMENTS

| EP | 2371333 A1 | 10/2011 |
| JP | 04-058951 A | 2/1992 |
| JP | 05-317358 A | 12/1993 |
| JP | 09-299402 A | 11/1997 |
| JP | 10-211232 A | 8/1998 |
| JP | 2007-130178 A | 5/2007 |
| JP | 2011-120661 A | 6/2011 |
| JP | 2014-110890 A | 6/2014 |

* cited by examiner

ABSORBENT ARTICLE

RELATED APPLICATIONS

The present application is a National Phase of International Application Number PCT/JP2016/056116, filed Feb. 29, 2016, and claims priority to Japanese Patent Application Number 2015-104888, filed May 22, 2015.

TECHNICAL FIELD

The present invention relates to an absorbent article, such as a sanitary napkin, disposable diaper or incontinence pad.

BACKGROUND ART

An absorbent article, for example, a sanitary napkin that absorbs excreted fluid such as menstrual blood, commonly includes a liquid-permeable top sheet disposed on the skin side of the wearer, a liquid-impermeable back sheet disposed on the clothing side, and an absorbent body provided between the top sheet and the back sheet.

It is important for the top sheet of the absorbent article to be soft with a satisfactory feel on the skin, since the top sheet is the section that contacts with the skin of the user.

In recent years, therefore, it has become common to employ a top sheet provided with multiple rows of ridged-shaped raised sections on the surface that contacts with the skin, and furrow sections provided in the spaces between adjacent raised sections, such top sheets having relatively soft raised sections that contact with the skin, and the raised sections easily fitting to the skin surface, so that the top sheet tends to feel softness.

Among such types of absorbent articles, for the purpose of further improving softness, there exist ones having a construction such as described in Patent Literature 1, for example, wherein through-hole sections passing through the thickness direction of the nonwoven fabric of the top sheet are provided in the furrow sections between the raised sections. Because the absorbent article described in Patent Literature 1 has increased freedom of movement of the raised sections of the top sheet and increased freedom of movement of the fibers due to the through-hole sections, the raised sections and fibers follow movement of the skin and allow the softness of the raised sections to be felt more easily, tending to result in a superior feel of the top sheet on the skin.

CITATION LIST

Patent Literature

[PTL 1] Japanese Unexamined Patent Publication HEI No. 9-299402

SUMMARY OF INVENTION

Technical Problem

However, the absorbent article described in Patent Literature 1 has the top sheet joined to the absorbent body at the perimeter sections of the through-hole sections using an adhesive, and since the perimeter sections of the through-hole sections are narrower than the thickness of the top sheet, the contact area of the perimeter sections with the absorbent body is very small.

Consequently, the joining force of the perimeter sections of the through-hole sections of the top sheet with the absorbent body is low and it is not possible to ensure the necessary joining strength, and therefore when force acts between the top sheet and absorbent body in the direction mutually separating them, due to bending or twisting of the absorbent article by movement of the user, for example, the joining between the top sheet and absorbent body is easily loosened and mutual separation is very highly likely to occur.

When this occurs, and joining between the top sheet and absorbent body is loosened resulting in their mutual detachment, excreted fluid entering from the user of the absorbent article has a notably reduced migration rate from the top sheet to the absorbent body, and the absorption performance as an absorbent article is greatly impaired.

The technical problem of the present invention is to provide an absorbent article that can absolutely minimize detachment between a top sheet and absorbent body, thereby allowing an absorption performance to be stably maintained, while maintaining a satisfactory feel on a skin of the top sheet.

Solution to Problem

In order to solve this problem, an absorbent article of the present invention provides the following.

(1) An absorbent article having a lengthwise direction, a widthwise direction and a thickness direction and including: a liquid-permeable top sheet; a liquid-impermeable back sheet; and an absorbent body disposed between the top sheet and the back sheet, wherein the top sheet has a first surface located on an opposite side from the absorbent body and a second surface on the absorbent body side, and includes: a plurality of raised sections protruding in a direction toward the first surface, which are extended in the lengthwise direction and formed at predetermined intervals in the widthwise direction, and a plurality of furrow sections depressed in a direction toward the second surface, which are extended in the lengthwise direction and formed between the raised sections, each of the furrow sections includes a first recess section including a first bottom section located further in a direction toward the absorbent body than a location of the first surface at a top section of each of the raised sections, and a plurality of second recess sections formed discontinuously in the lengthwise direction inside the first recess section and formed as depressions opening into the first bottom section, each of the second recess sections includes a perimeter wall section extending from the first bottom section in a direction toward the absorbent body, and a second bottom section formed on an edge of the perimeter wall section on the absorbent body side so as to plug the edge and having a highest fiber density in the top sheet, and in the each raised section, at least a portion of the second surface at the top section is not joined to the absorbent body, and in at least the each second recess section of the each furrow section, the second bottom section is joined to the absorbent body.

(2) The absorbent article according to (1) above, wherein at least a portion of the first bottom section is joined with a top sheet side portion of the absorbent body.

The first bottom sections are thus joined with the absorbent body, resulting in higher and more stable peel strength, and therefore an increased liquid absorption property. In addition, since the first bottom sections have lower fiber densities and are softer than the second bottom sections, they more readily deform than the second bottom sections and readily follow movement of the raised sections.

As a result, it is possible to obtain an absorbent article that has no impairment of the softness of the raised sections, and that is resistant to detachment between the first bottom section and the absorbent body.

(3) The absorbent article according to (2) above, wherein a distance between the portion of the second surface at the top section of the raised section and the top sheet side portion of the absorbent body is smaller than a distance between a portion of the first bottom section at the first surface that are nearest the absorbent body and the top sheet side portion of the absorbent body.

Thus, even when a shear force has been applied in the widthwise direction to the raised section of the top sheet, space between the raised section and absorbent body either deform or collapse and absorb the external force, such that the tensile force on the top sheet produced by rubbing with the skin of the wearer is reduced, and detachment of the top sheet from the absorbent body can be more reliably minimized.

(4) The absorbent article according to any one of (1) to (3) above, wherein the top sheet has a structure with at least two raised sections situated between one of the second recess sections and another of the second recess sections adjacent to the one second recess section in the widthwise direction.

Since the top sheet has the second recess sections joined to the absorbent body, tensile force can potentially be generated in the top sheet in the widthwise direction by joining of the second recess sections, but by having the first bottom sections that have lower fiber densities and are more easily deformable than the second bottom sections, situated between adjacent second bottom sections, it is possible to absorb the tensile force. In addition, even when an external force has acted on the raised sections in the widthwise direction, the first bottom sections absorb the external force, thus helping to minimize detachment of the top sheet from the absorbent body.

In addition, since the tensile force that can potentially be generated in the raised sections is absorbed by the first bottom sections, because the second bottom sections are joined to the absorbent body, the degree of freedom of the raised sections in the widthwise direction is not inhibited, allowing the softness of the raised sections to be stably maintained.

(5) The absorbent article according to any one of (1) to (4) above, wherein the top sheet has a portion that a structure in which the first recess section of one of the furrow sections and the first recess section of another of the furrow sections adjacent to the one furrow section are mutually adjacent, is continued over an entire width in the widthwise direction.

Thus, the top sheet has a structure wherein the first recess sections and raised sections are situated alternately across the entire width in the widthwise direction, and second recess sections joined to the absorbent body are not present between adjacent raised sections. As a result, the first bottom sections that have lower fiber densities and greater deformability than the second bottom sections cause the raised sections to follow movement of the wearer, allowing more stable fitting to the skin, while the raised sections can be caused to deform more flexibly, such that high softness can be ensured for the top sheet as a whole section.

(6) The absorbent article according to any one of (1) to (5) above, wherein the perimeter wall section has a pair of first perimeter wall sections formed along the lengthwise direction, and a pair of second perimeter wall sections formed along the widthwise direction, and includes hole sections passing through to the second surface in the pair of first perimeter wall sections.

Thus, the hole sections of the first perimeter wall sections of the perimeter wall sections can release the tension of fibers forming the adjacent raised sections, thereby increasing the freedom of movement of the raised sections as a whole section or the fibers forming the raised sections, and further increasing the softness of the raised sections.

(7) The absorbent article according to any one of (1) to (6) above, wherein the second surface of the second bottom section is formed flat.

Thus, contact areas of the second bottom sections with the absorbent body are increased, allowing joining regions with maximally large sizes to be ensured and allowing more stable peel strength to be ensured.

(8) The absorbent article according to any one of (1) to (7) above, wherein the top sheet has a structure in which a region of the first surface and a region of the second surface of the raised section are curved into shapes so as to be convex in a direction from the second surface toward the first surface, while a region of the first surface and a region of the second surface in the first recess section of the furrow section are curved into shapes so as to be convex in a direction from the first surface toward the second surface.

Since the raised sections and the first recess sections of the top sheet thus deform in the thickness direction and the widthwise direction in synchronization with the regions of the first surfaces and the regions of the second surfaces, it is possible to stably ensure softness of the raised sections as a whole section and the first recess sections as a whole section. In addition, since the raised sections and first recess sections readily deform under external force, it is possible to ensure more stable softness for the raised sections themselves or the first recess sections themselves, while more stably minimizing detachment from the absorbent body.

(9) The absorbent article according to any one of (1) to (8) above, further including, on a top sheet side surface, a compressed groove extending in the widthwise direction, wherein the top sheet and the absorbent body have been compressed in the thickness direction.

Thus, even when tensile force has been generated in the top sheet by compressing to form the compressed grooves, the second recess sections joined to the absorbent body can prevent or alleviate spreading of that tensile force, while the compressed grooves is provided to increase joining between the top sheet and absorbent body. Consequently, since the effect of tensile force on the first recess sections and on the raised sections adjacent to the first recess sections can be reduced, it is possible to minimize reduction in softness of the top sheet due to the effect of the compressed grooves, to reduce to a minimum any collapse of the shapes of the raised sections and first recess sections caused by the tensile force of compressing, and to also minimize contact of the skin with the second recess sections and maintain a satisfactory feel on the skin.

Advantageous Effects of Invention

According to the absorbent article of the present invention, the top sheet has no impairment of softness since the raised sections that are not joined to the absorbent body are able to freely move, while the second recess sections of the furrow sections are joined to the absorbent body at the second bottom sections, which have the highest fiber density within the top sheet. Thus, compared to the conventional technique, it is possible to more stably join the top sheet to the absorbent body and more stably minimize detachment of the top sheet from the absorbent body, to thereby minimize impairment of the fluid absorption property.

It is therefore possible to ensure both excellent feel on the skin and a high liquid absorption property, which are necessary for an absorbent article.

DESCRIPTION OF EMBODIMENTS

Figure 1:
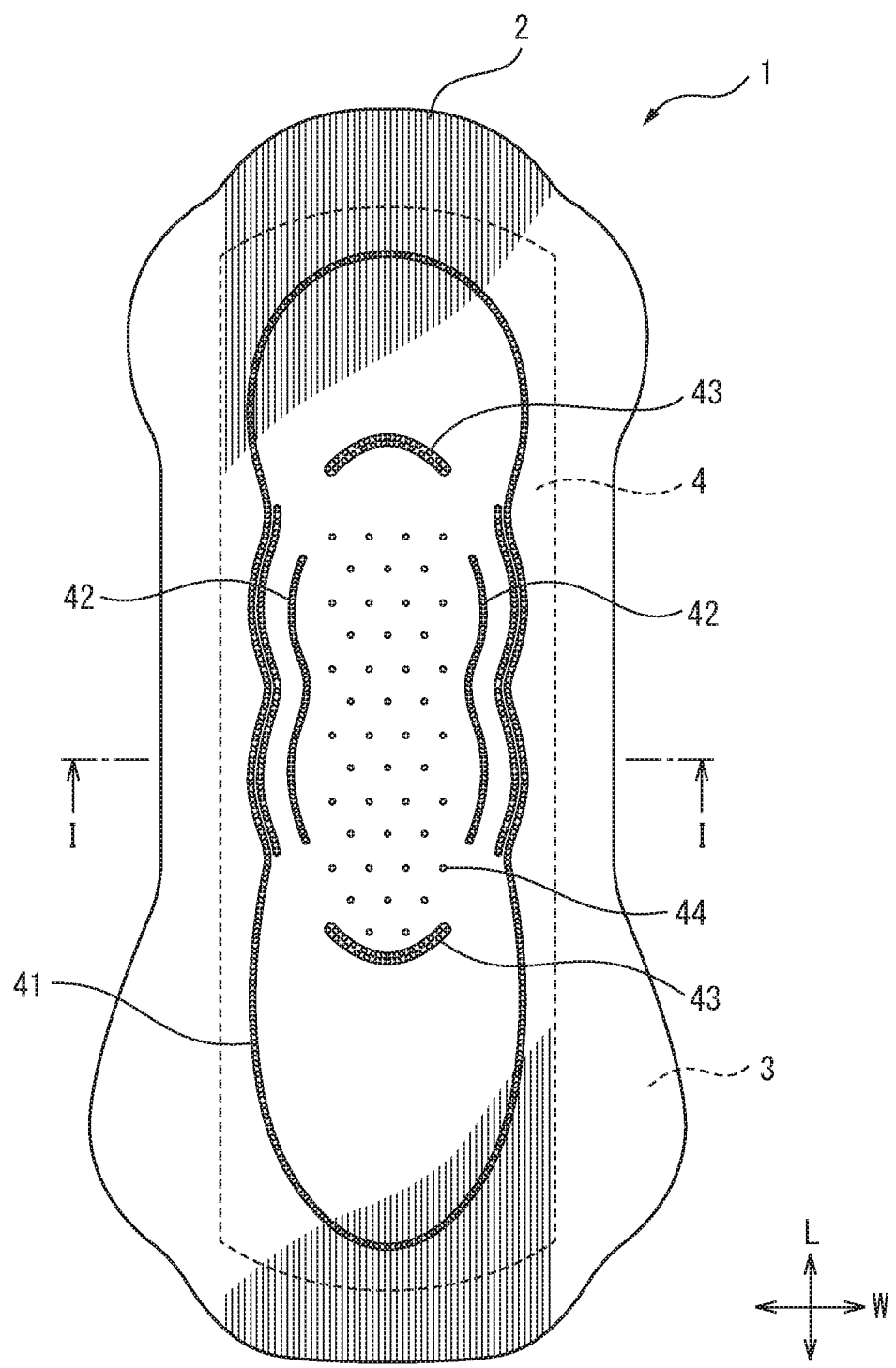
FIG. 1 is a plan view schematically showing a sanitary napkin as an embodiment of an absorbent article of the present invention.

FIG. 1 to FIG. 6 show an embodiment of an absorbent article of the present invention, and this embodiment will be explained in which the absorbent article is a sanitary napkin.

Specifically, a sanitary napkin 1 has a lengthwise direction (L), a widthwise direction (W) and a thickness direction (D) and includes a top sheet 2 as a liquid-permeable layer, a back sheet 3 as a liquid-impermeable layer disposed on one side of the top sheet 2, and an absorbent body 4 disposed between the top sheet 2 and the back sheet 3.

The back sheet 3 is provided with a pressure-sensitive adhesive sheet 5 to attach the sanitary napkin 1 to the crotch section of underwear.

The back sheet 3 is provided on the user's underwear side (the lower side of the absorbent body 4 in FIG. 2) of the sanitary napkin 1, serving to prevent permeation of excreted fluid that has been discharged and to prevent its leakage into underwear.

The back sheet 3 is mutually joined with the top sheet 2 at the perimeter section, while the absorbent body 4 is inserted between the back sheet 3 and the top sheet 2.

The absorbent body 4 serves to absorb excreted fluid such as menstrual blood, and for this embodiment, there is used one that contains an absorbent material that absorbs and retains excreted fluid. In addition, the absorbent body 4 is formed long in the direction along the lengthwise direction of the sanitary napkin 1, both end sides in the lengthwise direction being curved so as to be outwardly convex in the lengthwise direction of the absorbent body 4, and it is formed into an essentially oblong shape as viewed flat, that has a constant thickness and is smaller than the top sheet 2 or back sheet 3. In the absorbent body 4 of this embodiment, both the top sheet side surface and the back sheet side surface are formed in a flat manner.

The thickness, basis weight and so on of the absorbent body can be appropriately adjusted according to the properties desired for the sanitary napkin (for example, absorption property, strength and lightweight property). The thickness of the absorbent body will usually be 0.1 to 15 mm, preferably 1 to 10 mm and more preferably 2 to 5 mm, and the basis weight will usually be 20 to 1000 $g/m^2$, preferably 50 to 800 $g/m^2$ and more preferably 100 to 500 $g/m^2$. The thickness, basis weight and so on of the absorbent body may be constant across the entire absorbent body, or it may partially differ.

Furthermore, the absorbent body 4 has both the top sheet 2 on the top sheet side surface (the upper side of the absorbent body 4 in FIG. 2) and the back sheet 3 on the back sheet side surface (the lower side of the absorbent body 4 in FIG. 2) joined by an adhesive such as a hot-melt adhesive.

The top sheet 2 contacts the skin of the wearer and causes rapid absorption or penetration of excreted fluids from the wearer, causing them to migrate toward the absorbent body 4, and it is disposed on the side of the absorbent body 4 facing the skin of the wearer (the upper side of the absorbent body 4 in FIG. 1 to FIG. 6).

For this embodiment, the top sheet 2 is formed long in the direction along the lengthwise direction of the sanitary napkin 1.

The top sheet 2 is formed, for example, from a nonwoven fabric, woven fabric, synthetic resin film with liquid permeation holes or net-like sheet with meshes, and the nonwoven fabric is preferred among these.

For this embodiment, a nonwoven fabric containing thermoplastic resin fibers is used for increased strength of the top sheet 2.

According to the present invention, the thermoplastic resin composing the thermoplastic resin fibers may be a polyolefin, polyester, polyamide or the like. Examples of polyolefin include straight-chain low-density polyethylene (LLDPE), low-density polyethylene (LDPE), medium-density polyethylene (MDPE), high-density polyethylene (HDPE), polypropylene, polybutylene, and copolymers composed mainly of the foregoing (for example, ethylene-vinyl acetate copolymer (EVA), ethylene-ethyl acrylate copolymer (EEA), ethylene-acrylic acid copolymer (EAA) or an ionomer resin). Examples of polyester include polyesters of straight-chain or branched polyhydroxyalkane acids up to C20, such as polyethylene terephthalate (PET), polytrimethylene terephthalate (PTT), polybutylene terephthalate (PBT), polylactic acid and polyglycolic acid, copolymers composed mainly thereof, and copolymerized polyesters composed mainly of alkylene terephthalates copolymerized with a small amount of another component. Examples of polyamides include 6-nylon and 6,6-nylon. The diameter of the thermoplastic resin fibers will usually be 1.1 to 8.8 dtex and is preferably 2.2 to 5.6 dtex, while the fiber lengths will usually be 20 to 100 mm and are preferably 35 to 65 mm. The thermoplastic resin fibers may be subjected to hydrophilicizing treatment, the hydrophilicizing treatment being, for example, treatment utilizing a surfactant, hydrophilic agent or the like (for example, kneading of a surfactant into the fiber interiors, or coating of the fiber surfaces with a surfactant).

As shown in FIG. 3 to FIG. 5 and FIG. 11, the top sheet 2 includes a first surface 2a located on the side opposite the absorbent body 4, and a second surface 2b on the absorbent body 4 side which is the side opposite the first surface 2a.

In addition, the top sheet 2 has a plurality of raised sections 11 extended in the lengthwise direction and formed at predetermined intervals in the widthwise direction, which protrude in the direction toward the first surface 2a and a plurality of furrow sections 12 extended in the lengthwise direction and formed between the raised sections 11, which are depressed in the direction toward the second surface 2b.

The furrow section 12 has a first recess section 21 including a first bottom section 22 located further in the direction toward the absorbent body 4 than the location of the first surface 2a at the top section 13 of the raised section 11, and a plurality of second recess sections 26 each provided in a discontinuous manner in the lengthwise direction inside the first recess section 21, and formed as a depression opening into the first bottom section 22.

Also, the second recess section 26 includes a perimeter wall section 27 extending in the direction from the first bottom section 22 toward the absorbent body 4, and a second bottom section 28 having the highest fiber density of the top sheet 2, provided at the edge of the perimeter wall section 27 on the absorbent body 4 side, so as to plug the edge.

Also, in the top sheet 2, the raised sections 11 do not have their second surfaces 2b joined to the absorbent body 4 at the top sections 13, but the furrow sections 12 have the second bottom sections 28 of the second recess sections 26 joined to the top sheet side portion of the absorbent body 4 (for this embodiment, the top sheet side surface of the absorbent body 4), by a layer 6 of the aforementioned adhesive.

Figure 4:
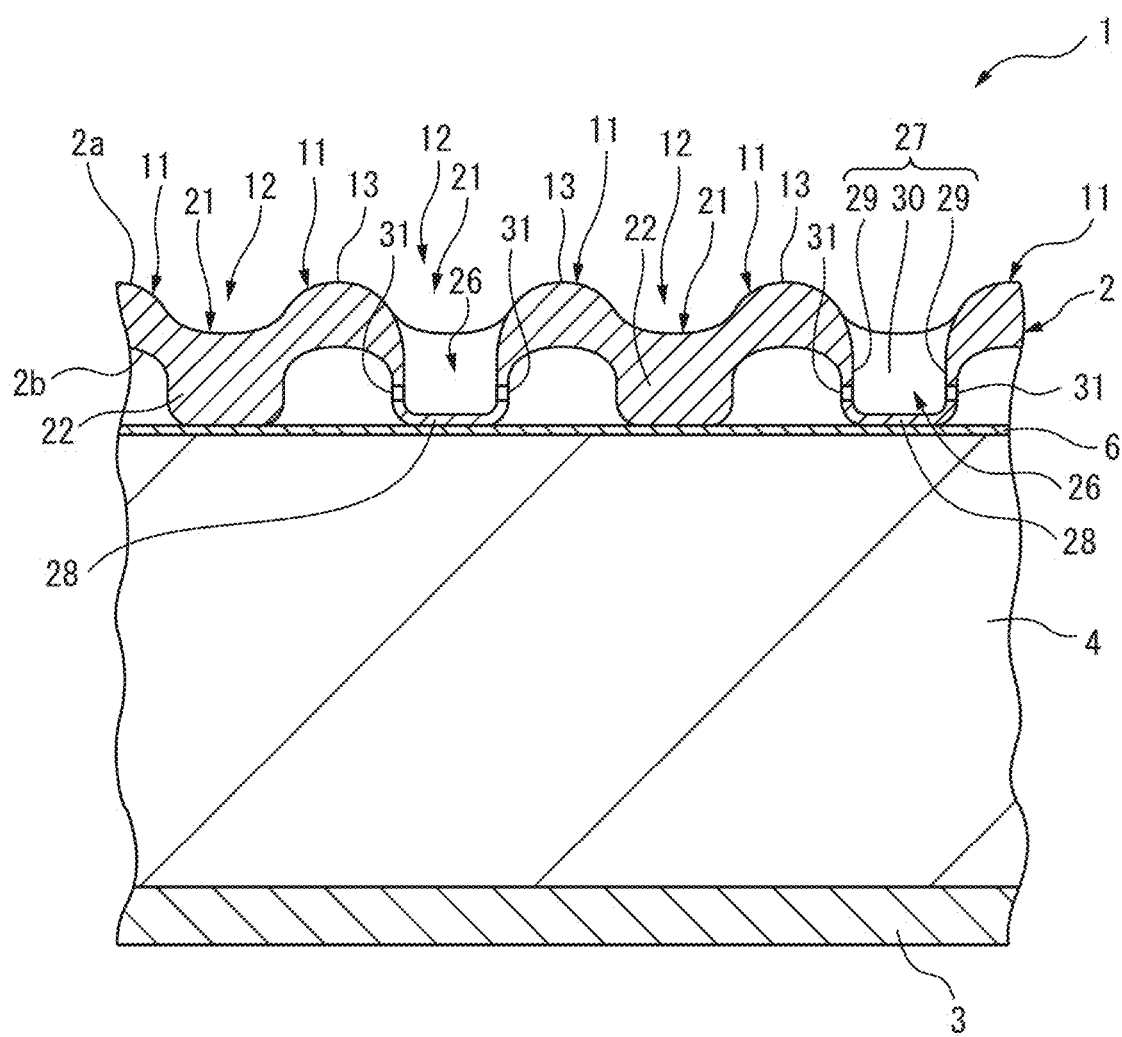
FIG. 4 is a schematic magnified cross-sectional view along line II-II of FIG. 3.
Figure 5:
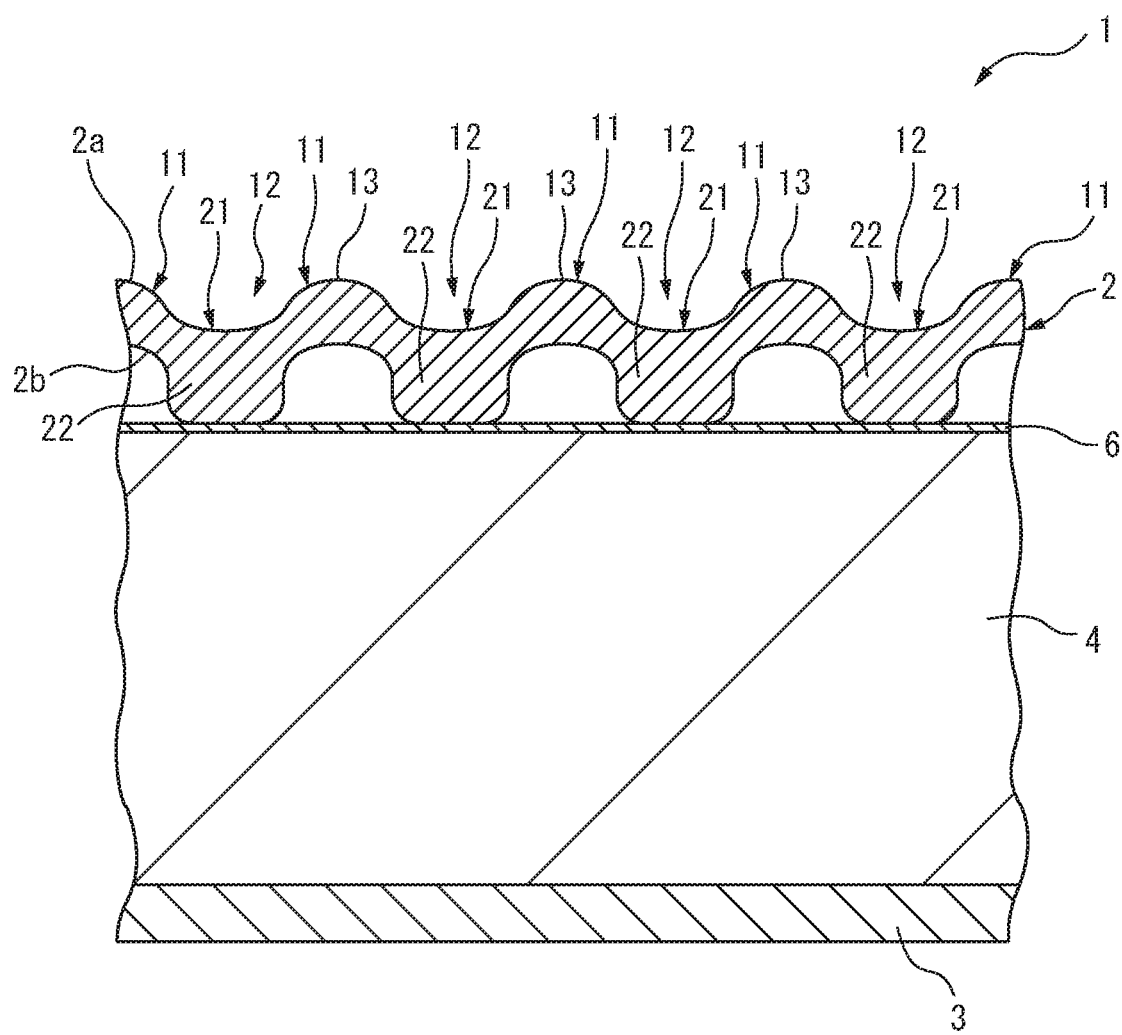
FIG. 5 is a schematic magnified cross-sectional view along line of FIG. 3.
Figure 6:
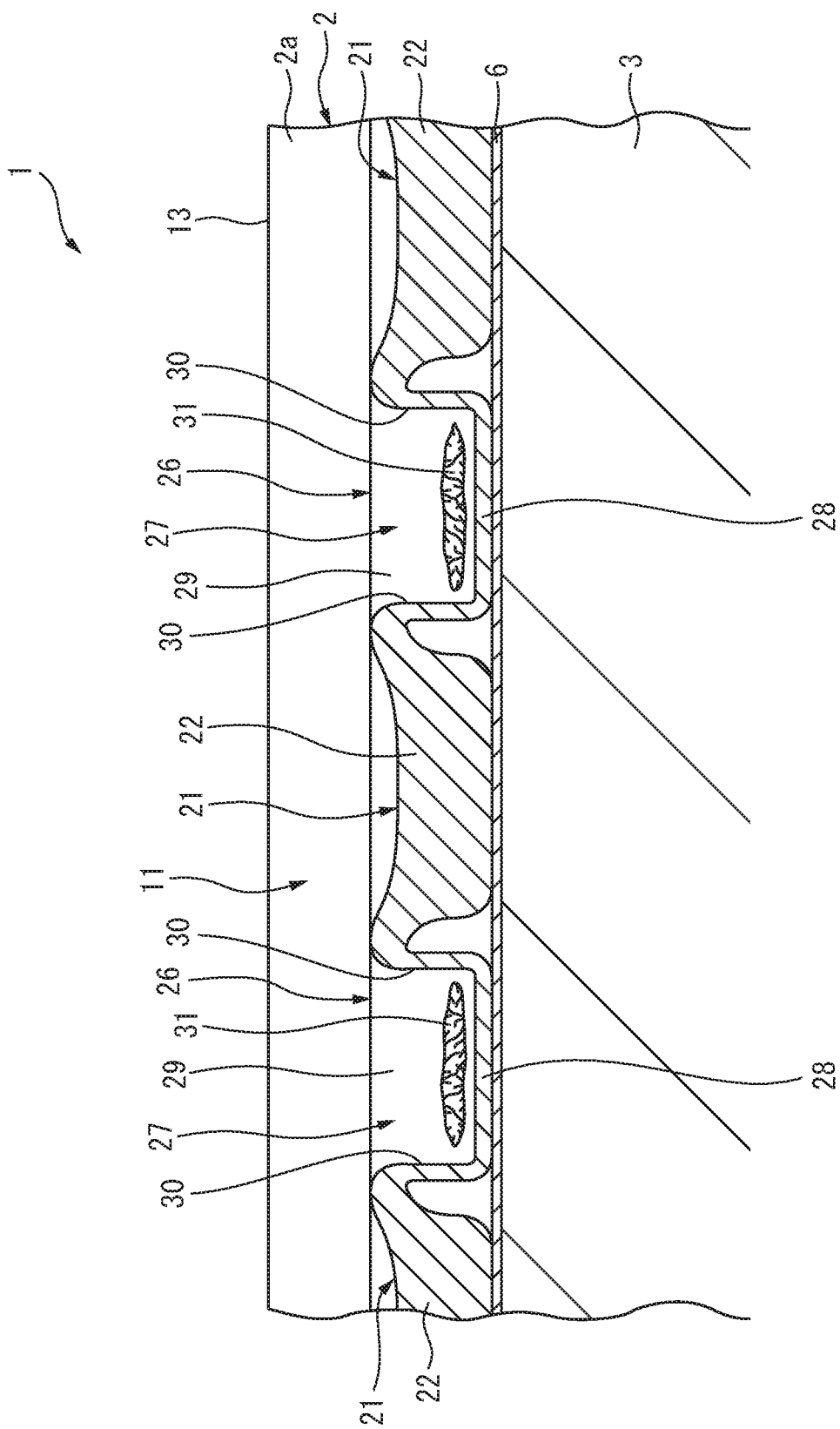
FIG. 6 is a schematic magnified cross-sectional view along line IV-IV of FIG. 3.
Figure 7:
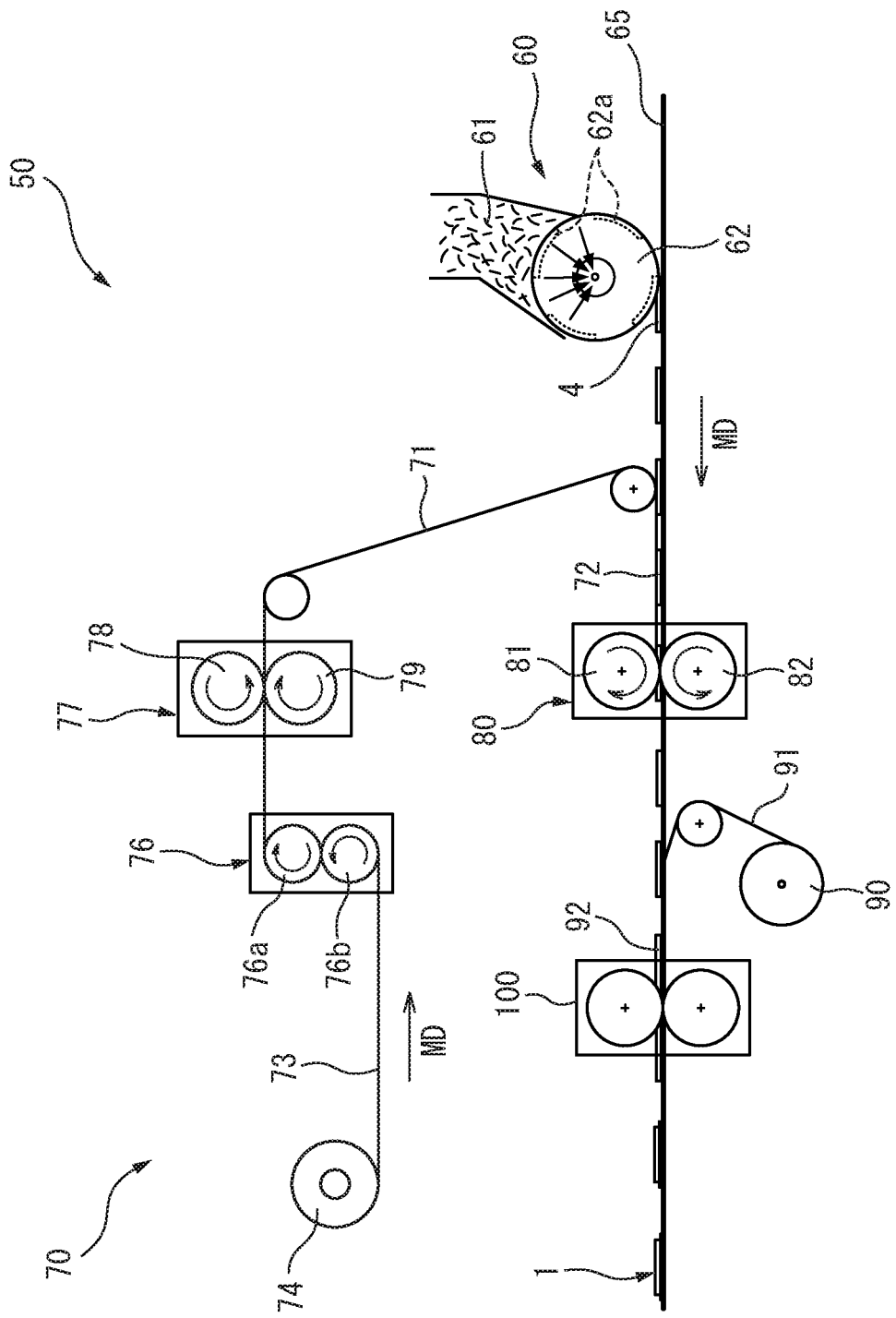
FIG. 7 is a view schematically showing a production apparatus of producing of an absorbent article according to the present invention.

Also for this embodiment, as shown in FIGS. 4 to 6, portions of the second surfaces 2b of the first bottom sections 22 of the first recess sections 21 are also joined to the top sheet side portion of the absorbent body 4 by the layer 6 of the adhesive, while the raised sections 11 do not have the portions of the second surfaces 2b, including the top sections 13, joined to the absorbent body 4.

Figure 11:
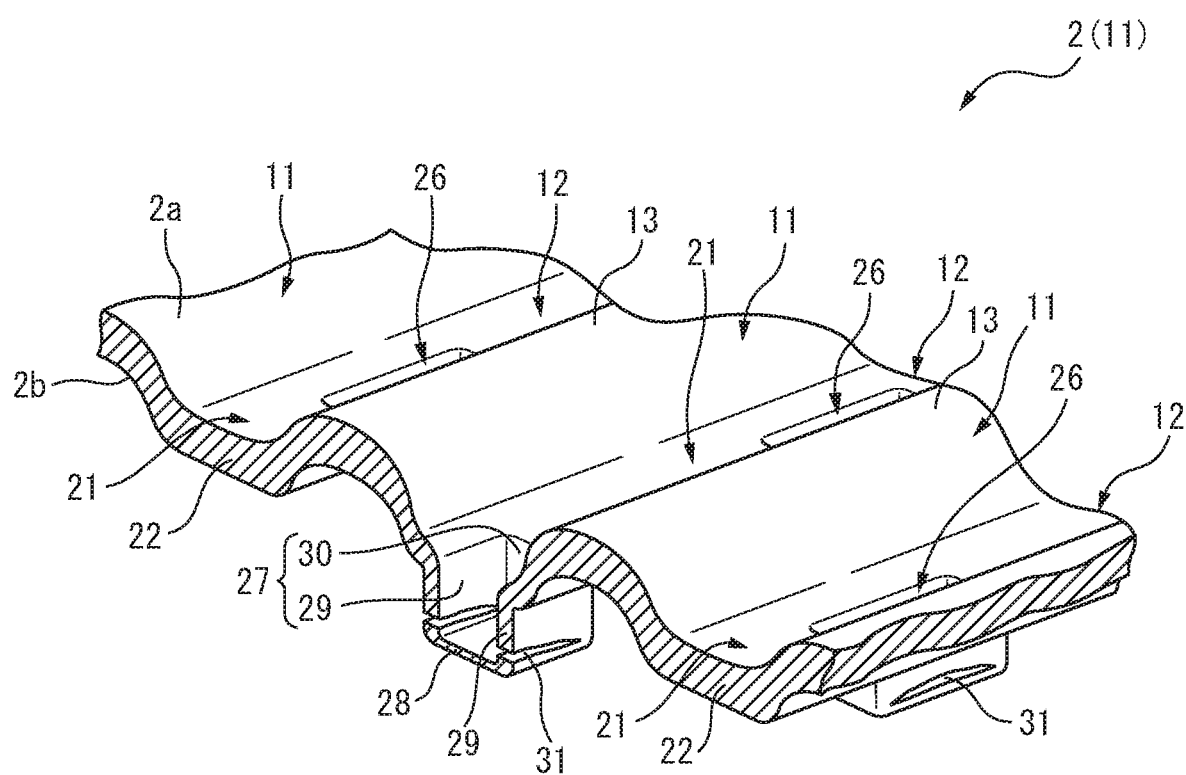
FIG. 11 is a partial cutaway perspective view of a top sheet (continuous top sheet) to be used for an absorbent article of the present invention.

As shown in FIG. 4, FIG. 5 and FIG. 11, the top sheet 2 of this embodiment has a structure in which the region of the first surface 2a and the region of the second surface 2b forming the raised section 11 are curved into convex shapes in the direction from the second surfaces 2b toward the first surfaces 2a (i.e. in the direction toward the side opposite the absorbent body 4). On the other hand, the first recess section 21 of the furrow section 12 has a structure in which the region of the first surface 2a and the region of the second surface 2b forming the first recess section 21 are curved into convex shapes in the direction from the first surface 2a toward the second surface 2b (i.e. the direction toward the absorbent body 4). The top sheet 2 is therefore a sheet having an essentially wavy cross-section with alternately repeating concavo-convexities with respect to the widthwise direction.

The raised sections 11 are extended in the lengthwise direction of the sanitary napkin 1, i.e. in the lengthwise direction of the top sheet 2, while being arranged in rows with predetermined intervals in the widthwise direction of the top sheet 2. For this embodiment, each of the raised sections 11 is extended continuously in the lengthwise direction, so as to be mutually parallel with the other raised sections 11.

The raised section according to the present invention has the interval with the other adjacent raised section of preferably 0.25 to 5 mm, more preferably 0.5 to 3 mm and even more preferably 0.75 to 2 mm. Here, the interval between adjacent raised sections is the distance between approximately the center locations of the respective raised sections in the widthwise direction of the top sheet (essentially the top sections of the raised sections).

If the distance of the interval between adjacent raised sections is less than 0.25 mm, the nonwoven fabric cannot be considered to have formed a concavo-convex structure and the contact area with the skin cannot be significantly reduced by the raised sections, and therefore the feel on the skin may potentially be impaired, while conversely if it is greater than 5 mm, the difference with the nonwoven fabric to be processed will not be sufficiently large, making it impossible to obtain a soft feel on the skin using the concavo-convexities.

Also, as shown in FIG. 4, the distance between the portion of the second surface 2b at the top section 13 of the raised section 11 and the top sheet side portion of the absorbent body 4 is smaller than the distance between the portion of the first surface 2a of the first bottom section 22 nearest the absorbent body 4 and the top sheet side portion of the absorbent body 4. This is therefore a mode in which the top sections 13 of the raised sections 11 are disposed, overall, at locations more distant from the absorbent body 4 (the upper side in FIG. 4) than the first surfaces 2a of the first bottom sections 22.

Since spaces are thus stably formed between the second surfaces 2b of the raised sections 11 and the top sheet side surface of the absorbent body 4, even if the raised sections 11 of the top sheet 2 are subjected to external force from the wearer, particularly shear force in the widthwise direction accompanying friction with the skin of the wearer, the force can be easily absorbed by the raised sections 11 deforming or collapsing, depending on the direction and size of the external force. Moreover, when the raised sections 11 have collapsed, the difference in the heights of the first surfaces 2a of the raised sections 11 and the first surfaces 2a of the first recess sections 21 is reduced. Thus, tensile force of the top sheet 2 generated by friction between the top sheet 2 and the skin of the wearer is reduced, and detachment of the top sheet 2 from the absorbent body 4 can be more reliably avoided.

The first recess sections 21 are formed integrally with the raised sections 11 in the widthwise direction. Moreover, the thickness at the largest portion of the first bottom section 22 of the first recess section 21 is thickest in the top sheet 2, while the first bottom section 22 is a section with excellent elasticity. The plurality of first recess sections 21 formed in the top sheet 2 are all formed with mutually equal widths.

For this embodiment, the second surfaces 2b of the first bottom sections 22 of the first recess sections 21 are joined to the top sheet side portions of the absorbent body 4, at least at the portions of the first bottom sections 22 located furthest to the top sheet side, i.e. the portions located at a depth most distant from the locations of the heights of the top sections 13 of the raised sections 11, and their proximal portions.

The second recess section 26 has an essentially rectangular opening as viewed flat (as viewed from the first surface 2a of the top sheet 2), and protrudes overall to the absorbent body 4 side of the top sheet 2, defining an essentially cuboid interior space. Also, the second recess sections 26 are disposed at a constant interval in the lengthwise direction of each furrow section 12, more specifically the lengthwise direction of each first recess section 21, and each second recess section 26 is formed in a mutually independent manner from the other second recess sections 26.

The perimeter wall section 27 has a pair of first perimeter wall sections 29, 29 formed along the lengthwise direction of the top sheet 2 and a pair of second perimeter wall sections 30, 30 formed along the widthwise direction of the top sheet 2. The pair of first perimeter wall sections 29, 29 are disposed at mutually facing locations, while the pair of second perimeter wall sections 30, 30 are also disposed at mutually facing locations.

As shown in FIG. 4 and FIG. 5, the pair of first perimeter wall sections 29, 29 have hole sections 31 formed in them passing through from the interior space of the first recess section 21 toward the second surfaces 2b.

According to this embodiment, one hole section 31 is provided for each of the pair of first perimeter wall sections 29, 29, and the hole section 31 is formed at a location near the second bottom section 28 of the first perimeter wall section 29 (and therefore two hole sections 31 are present for each second recess section 26). On the other hand, the pair of second perimeter wall sections 30, 30 do not have corresponding hole sections 31, and each second perimeter wall section 30 has its entire edge on the absorbent body 4 side directly connected to the second bottom section 28.

The second recess sections 26 are provided in the top sheet 2 in order to reduce to a minimum the likelihood that the bottoms of the furrow sections 12, and more specifically the first bottom sections 22 of the first recess sections 21, will contact the skin, and in order to minimize the contact area even when the first bottom sections 22 have contacted with the skin.

That is, according to the invention, the skin is most easily contacted by the raised sections of the top sheet and then by the first bottom sections of the first recess sections, but since the raised sections (especially the top sections) not joined to the absorbent body have the highest degree of softness, it is preferred for the raised sections to be given more opportunity to contact with the skin than the first bottom sections, and the top sheet with less contact area touching with the skin tends to feel softer. Consequently, by providing second recess sections in order to form portions without first recess sections, there will be still fewer portions in contact with the skin at the first bottom sections of the first recess sections, and the opportunity for and contact area of skin contact will be maximally reduced.

In addition, the second recess sections are provided at the first bottom section in order to provide second recess sections in the first bottom section of the first recess section which are less likely to contact the skin than the raised sections, so that the likelihood of the second recess sections contacting the skin will be absolutely minimized and any uncomfortable feeling or sensation of foreign matter caused by the second recess sections will be as little noticeable as possible.

One reason for providing the hole sections 31 on the first perimeter wall sections 29 for this embodiment is in order to release the tensile force of the fibers of the raised sections 11 adjacent to the furrow section 12 provided with the hole sections 31, thus increasing the freedom of movement of the raised sections 11 as a whole section or of the fibers forming the raised sections 11, and to improve the softness of the raised sections 11, more specifically the softness of the raised sections 11 in the thickness direction of the top sheet 2, as well as the softness when the skin is slid in the lengthwise direction or widthwise direction (especially the widthwise direction) of the top sheet 2, to ensure a smooth feel. This can provide the raised sections 11 with both an excellent hard/soft feeling (excellent softness in the thickness direction) and an excellent rough/smooth feeling in the lengthwise direction and widthwise direction (excellent smoothness on the front surface of the top sheet 2 (particularly the widthwise direction)), to allow an excellent hard/soft feeling and rough/smooth feeling to be ensured for the top sheet 2 as a whole section, thereby allowing a soft feel on the skin to be achieved.

Conversely, hole sections 31 are not provided on the second perimeter wall sections 30 so that the level differences, created by the presence of the second recess section 26, will be less likely to catch on the skin when the skin is slid in the lengthwise direction of the top sheet 2, i.e. in the direction in which the raised sections 11 or furrow section 12 are extended, to ensure smoothness in the lengthwise direction of the top sheet 2. That is, since the second perimeter wall sections are continuous with the first bottom sections 22 and second bottom sections 28 and integral without seams, the skin does not significantly sense the level difference of the first bottom sections 22 in the second recess sections 26 and smoothly and easily moves along the raised section 11 and furrow section 12, when the skin is slid in the lengthwise direction of the top sheet 2. This can ensure smoothness in the lengthwise direction of the top sheet 2 due to the softness of the raised sections 11 or softness of the fibers.

In addition, the hole sections 31 are provided at locations of the first perimeter wall sections 29 near the second bottom section 28 in order for the hole sections 31 to be as far as possible from the raised section 11 or first bottom sections 22 that tend to contact the skin, thereby minimizing opportunity for the hole sections 31 to contact the skin and reducing any uncomfortable feeling or sensation of foreign matter. This can more stably ensure smoothness when the skin has been slid in the planar direction of the nonwoven fabric.

Furthermore, as shown in FIG. 6, the hole sections 31 are formed by breaking the thermoplastic resin fibers contained in the top sheet 2 and not by melting of the thermoplastic resin fibers, and the perimeters of the hole sections 31 include, among the thermoplastic resin fibers, the broken ends of broken fibers having broken ends formed by breaking of the thermoplastic resin fibers. The broken ends of the broken fibers are formed by breaking, accomplished by pulling or physical cutting in the lengthwise direction of the thermoplastic resin fibers, and instead of being melted and rounded fiber ends with increased fiber diameters, as when thermoplastic resin fibers have melted, they are in a tapered state formed by tearing, or else have virtually no change in fiber diameter.

Thus, even when the skin of the wearer has been contacted with the perimeters of the hole sections 31, the absence of thermoplastic resin fibers hardened by melting reduces any uncomfortable feeling due to stiffness or catching of the fibers and minimizes any feeling of hardness or roughness from the top sheet 2.

Some of the fibers among the thermoplastic resin fibers span across the interior spaces of the hole sections 31. Also, some of the broken fibers have their broken ends extending into the interior spaces of the hole sections 31.

In addition, the interior space of the hole section 31 has a combination of thermoplastic resin fibers spanning across the interior space and thermoplastic resin fibers extending into the interior spaces, so that the space are not completely open. Thus, since the hole sections 31 have some of the thermoplastic resin fibers spanning across, or extending into, the interior spaces, even if the skin has contacted the hole sections 31, the thermoplastic resin fibers in the interior spaces can reduce the level differences between the first perimeter wall sections 29 or the second bottom sections 28 of the second recess sections 26, and the hole sections 31, to minimize any difference in touch sensation and to reduce any uncomfortable feeling for the person contacted.

Incidentally, the open area percentage of the interior space of the hole section is preferably 1 to 50%, more preferably 1.5 to 35% and even more preferably 2.5 to 20%.

If the open area percentage of the interior space of the hole section is less than 1% the open area percentage will be too low, making it impossible to impart freedom to the raised sections or the fibers of the raised sections, or to adequately ensure softness for the raised sections. If it is 50% or greater, conversely, the strength of the first perimeter wall sections in which the hole sections are formed will tend to be reduced, and the borders of the perimeters of the hole sections may potentially be felt. However, the open area percentage of the interior space of the hole section may be outside of this range, and set as desired, depending on the type of absorbent article and its purpose of use, etc.

In addition, the second bottom sections 28 are formed by the fibers composing the top sheet 2 being compressed in the direction from the first surfaces 2a toward the second surfaces 2b, and have the highest fiber density of the top sheet 2, as mentioned above, as well as the highest rigidity. In addition, the first surfaces 2a of the second bottom sections 28 (i.e. the interior side surfaces of the second recess sections) and the second surfaces 2b (i.e. the absorbent body 4 side surfaces) are formed in an essentially planar manner overall. For this embodiment, the sides of the second surfaces 2b of the second bottom sections 28 are essentially flat, and are in contact with the top sheet side surface of the absorbent body 4.

Since the second surfaces 2b of the second bottom sections 28 are thus flat, it is possible to maximally increase the contact area between the second bottom sections 28 and the absorbent body 4, thereby making it possible to ensure that the joining regions are as large as possible between the second surfaces 2b of the second bottom sections 28 and the top sheet side surface of the absorbent body 4. As a result, the top sheet 2 is even less likely to detach from the absorbent body 4, and migration of excreted fluids between the top sheet 2 and the absorbent body 4 can proceed more smoothly.

Since as mentioned above, particularly for this embodiment, the top sheet side surface of the absorbent body 4 is a flat surface, the sides of the second surfaces 2b of the second bottom sections 28 are mutually joined with their surfaces in contact with the top sheet side surface of the absorbent body 4. Thus, even more stable joining of the top sheet 2 with the absorbent body 4 is maintained, rendering them less likely to become detached from each other, and migration of excreted fluids between the top sheet 2 and the absorbent body 4 can be accomplished very smoothly.

Figure 3:
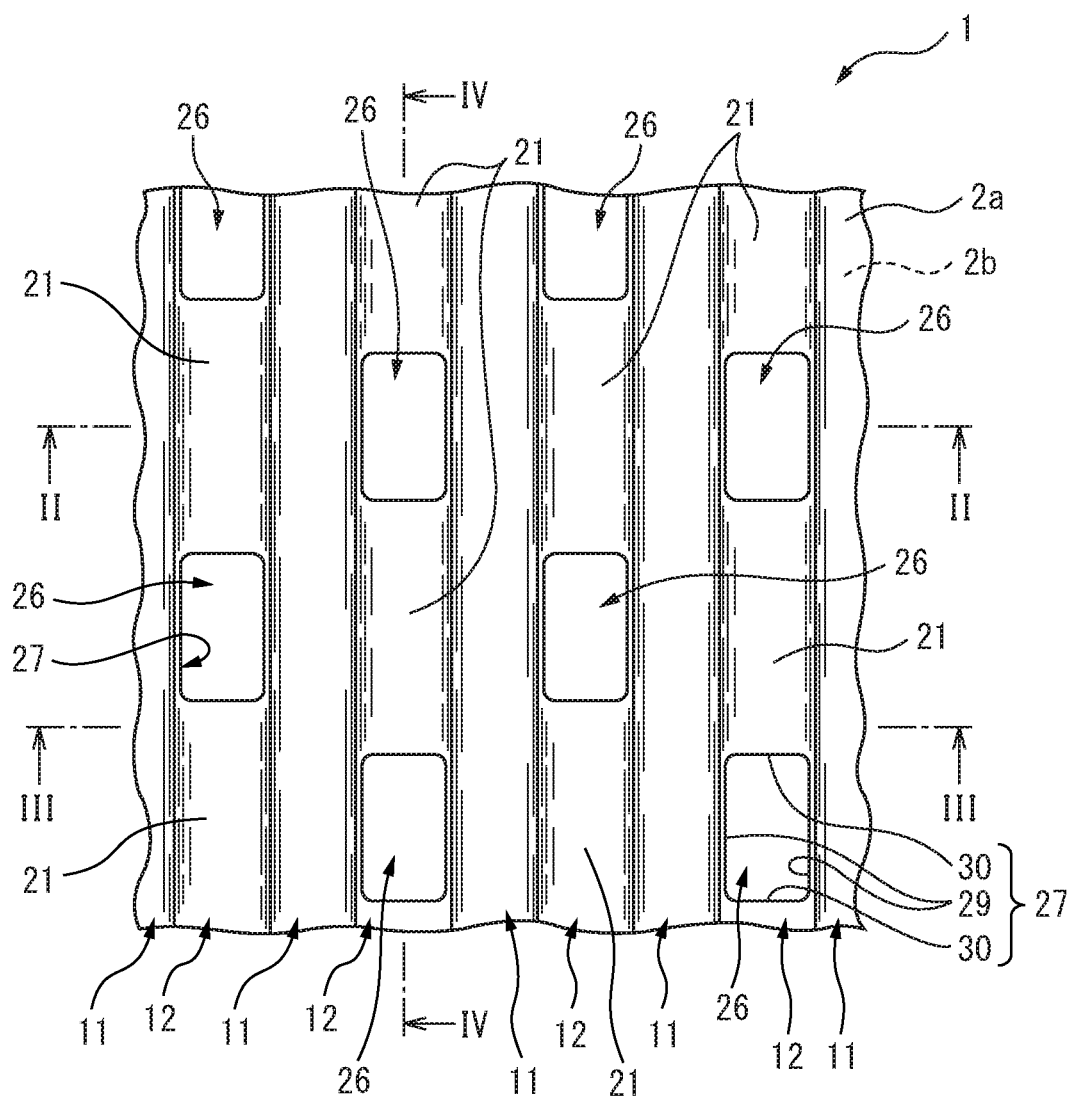
FIG. 3 is a partial magnified plan view of FIG. 1.

As shown in FIG. 3, for this embodiment the second recess sections 26 are disposed in a zigzag fashion on the top sheet 2 as viewed flat (as viewed in the thickness direction).

Also, as shown in FIG. 4, the top sheet 2 has a structure in which at least two raised sections 11 are situated between a second recess section 26 and another second recess section 26 adjacent to the second recess section 26 in the widthwise direction. That is, the top sheet 2 has a structure with a raised section 11, first recess section 21 and raised section 11 disposed in that order, between a second recess section 26 and its adjacent second recess section 26 in the widthwise direction.

The top sheet 2 is structured in this manner in order to more stably minimize detachment of the top sheet 2 from the absorbent body 4, and to maintain the softness of the raised sections.

In other words, since the top sheet 2 has the second recess sections 26 joined to the absorbent body 4, tensile force can potentially be generated in the widthwise direction on the top sheet 2 due to joining of the second recess sections 26 with the absorbent body. Consequently, since the first bottom sections 22 which have lower fiber density than the second bottom sections 28 and are more easily deformable than the second bottom sections 28 are situated between adjacent second bottom sections 28, 28, it is possible to absorb the tension by deformation of the first bottom sections 22. This allows the softness of the raised sections 11 to be stably maintained without interfering with freedom of the raised sections 11 in the widthwise direction.

Also, even when external force has acted on the raised sections 11 in the widthwise direction, the external force can be absorbed by deformation of the first bottom sections 22, and therefore the action of large force to the second bottom sections 28 by the external force is reduced and detachment of the second bottom sections 28 from the absorbent body 4 is inhibited, and as a result detachment of the top sheet 2 from the absorbent body 4 is inhibited.

Furthermore, as shown in FIG. 5, in the top sheet 2, the structure in which a first recess section 21 of the furrow section 12 and a first recess section 21 of other furrow section 12 adjacent to that furrow section 12 are mutually adjacent has a portion that is continuous over the entire width in the widthwise direction. That is, the top sheet 2 has a structure with a first recess section 21, raised section 11 and first recess section 21 disposed in that order across the entire width in the widthwise direction, and a portion where a second recess section 26 is not present.

This is because in the top sheet 2, as mentioned above, the second recess sections 26 are disposed in a zigzag fashion while the intervals between the second recess sections 26 in the lengthwise direction are set wider than the sizes of the second recess sections 26 in the lengthwise direction.

The structure in which the first recess section 21 of the furrow section 12 and the first recess section 21 of other furrow section 12 adjacent to that furrow section 12 are mutually adjacent is made continuous across the entire width in the widthwise direction of the top sheet 2 in this manner, in order to utilize the ease of deformation of the first bottom sections 22 of the first recess sections 21 to impart higher softness to the raised sections. That is, by the structure of the top sheet 2 in which the first recess sections 21 and raised sections 11 are alternately arranged across the entire width in the widthwise direction and no second recess section 26 joined to the absorbent body 4 are present between adjacent raised sections 11, the first bottom sections 22 that have lower fiber density than the second bottom sections 28 and deform more easily than the second bottom sections 28 cause the raised sections 11 to follow movement of the wearer, and therefore the raised sections fit more stably onto the skin. Furthermore, since the softness of the first bottom sections 22 is utilized to allow the raised sections 11 to also deform more flexibly, it is possible to ensure even higher softness for the top sheet 2 as a whole section.

Figure 2:
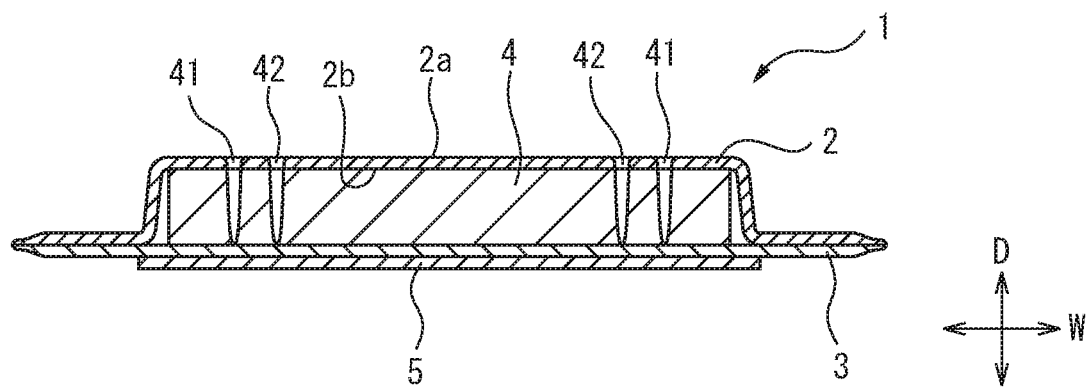
FIG. 2 is a schematic cross-sectional view along line I-I of FIG. 1.

Incidentally, as shown in FIG. 1 and FIG. 2, the sanitary napkin 1 of this embodiment includes, on the top sheet side surface, a plurality of compressed grooves 41-43 formed by compressing the top sheet 2 and absorbent body 4 by the emboss process in the thickness direction.

Of the plurality of compressed grooves, as viewed flat (when viewed from the thickness direction), the sanitary napkin 1 of this embodiment is provided with an annular first compressed groove 41 formed long as a whole section in the lengthwise direction of the sanitary napkin 1, located on the outermost side, and a pair of second compressed grooves 42, 42 extending in the lengthwise direction, located on the inner side of the first compressed groove 41 and located at about the center in the lengthwise direction. It is also provided with a pair of third compressed grooves 43, 43 extending in the widthwise direction, being located on the inner side of the first compressed groove 41 and located near both end sides in the lengthwise direction of the first compressed groove 41.

The compressed grooves 41-43 are provided in order to create more firm bonding between the top sheet 2 and the absorbent body 4 by compressing of the compressed grooves 41-43. They also serve to increase the fiber density between the top sheet 2 and the absorbent body 4, and to increase uptake of excreted fluids from the top sheet 2 to the absorbent body 4.

Generally speaking, when a top sheet and absorbent body are compressed in the thickness direction to form compressed grooves, the compressed grooves have the top sheet in a state that is stretched in the direction toward the absorbent body, and therefore if some countermeasure is not taken, tensile force is generated in the top sheet, and especially the raised sections, causing stiffness, while the raised sections deform and tend to have reduced softness. This tendency is especially prominent near the compressed grooves.

According to the present invention, however, the second recess sections of the furrow sections of the top sheet joined to the absorbent body prevent or alleviate the spread of tensile force generated in the top sheet by compressing of the compressed grooves, thus reducing the effect of the tensile force on the raised sections or first recess sections.

In other words, when tensile force is generated in the top sheet by compressing, the perimeter wall sections of the second recess sections deform while the second bottom sections are joined to the absorbent body, thereby buffering the tensile force and preventing its spread to other portions or alleviating the tension to prevent its spread to other portions. This reduces to a minimum the effect of the tensile force generated on the top sheet by compressing, and the top sheet is less affected by deformation, except for the portions that are significantly affected by the compressing, while less stiffness also results from the tensile force.

According to the present invention, therefore, it is possible to minimize reduction in softness of the top sheet by the effects of the compressed grooves while more firmly joining the top sheet and the absorbent body by the compressed grooves, and to also reduce to a minimum any collapse of the raised sections or first recess sections due to the tensile force of compressing, and maintain a satisfactory feel on the skin for the top sheet. Furthermore, since collapse of the shapes of the raised sections and first recess sections is reduced, it is possible to minimize the opportunity for contact of the second recess sections with the skin, and in this regard as well, reduction in feel on the skin is minimized.

Furthermore, for this embodiment, the structure is such that the perimeter wall section 27 is cut out by the hole sections 31 formed in the perimeter wall section 27 of the second recess section 26 in the furrow section 12 of the top sheet 2, and therefore the perimeter wall section 27 as a whole section is flexible and deformable, and tensile force acting on the top sheet 2 can be easily buffered. Furthermore, since the hole sections 31 release the tensile force of fibers of the furrow section 12 and their adjacent raised sections 11 and improve the freedom of movement of the raised sections 11 as a whole section or the fibers forming the raised sections 11, as mentioned above, it is easy to alleviate tensile force acting on the top sheet 2. This makes it possible to effectively prevent tensile force generated in the lengthwise direction or widthwise direction of the top sheet 2 by compressing of the compressed grooves, from spreading to other portions. The effect of the tensile force can therefore be even more stably inhibited.

For this embodiment, as shown in FIG. 1, a plurality of dotted compressed sections 44 are formed by compressing the top sheet 2 and the absorbent body 4, at portions surrounded by second compressed grooves 42, 42 and third compressed grooves 43, 43 on the top sheet side of the sanitary napkin 1, i.e. at essentially the center of the top sheet 2. Similar to the compressed grooves 41-43, these compressed sections 44 can also create tensile force in the top sheet 2 by compressing, but as mentioned above, the effect of the tensile force created by compressing can be reduced by the function of the second recess sections 26.

Furthermore, the thickness of the compressed sections of the compressed grooves 41-43 or compressed sections 44 will depend on the thickness of the top sheet or the absorbent body, but for example, the thickness of the compressed sections is preferably less than 20%, more preferably no greater than 5% and even more preferably no greater than 3% of the thickness of the absorbent body.

If the thickness of the compressed sections is equal to or greater than 20% of the thickness of the absorbent body, the stamping may be insufficient and the desired fiber density may not be obtained, and therefore uptake of excreted fluids may be reduced and the strength against detachment may be weakened. The depths of each of the compressed grooves 41-43 and compressed sections 44 may be the same depth, or mutually different depths.

An example of a method of producing a sanitary napkin having such a structure will now be described.

In the method of producing a sanitary napkin 1 according to this embodiment, there are carried out in order a step of forming an absorbent body, a step of laminating a continuous top sheet, formed in a step of forming a long continuous top sheet to be a top sheet as described below, on the absorbent body to form a lamination body of the continuous top sheet and the absorbent body, and a step of forming compressed grooves in the lamination body. There are also carried out in order a step of laminating a long continuous back sheet to be a back sheet on the lamination body to form a continuous sanitary napkin, and a cutting step of cutting out units of a sanitary napkin from the continuous sanitary napkin.

A production apparatus 50 such as shown in FIG. 7 to FIG. 10, for example, is used for producing the sanitary napkin 1.

The production apparatus 50 includes an absorbent body-forming apparatus 60 provided with a freely rotating suction drum 62 that forms an absorbent body 4 by lamination of an absorbent body material 61, a top sheet-forming apparatus 70 that forms a continuous top sheet 71 that is to serve as the top sheet 2, and an embossing apparatus 80 that compresses the top sheet 2 and absorbent body 4 by embossing to form stamped grooves 41-43. It further includes a back sheet roll 90 on which the continuous back sheet 91 that is to be the back sheet 3 is wound as a roll, and a cutting apparatus 100 that cuts the continuous sanitary napkin 92, in which the continuous top sheet 71 and continuous back sheet 91 are attached to the absorbent body 4, to form individual sanitary napkins 1.

In the step of producing the absorbent body, at the absorbent body-forming apparatus 60, the absorbent body material 61 is supplied from above onto the outer peripheral surface of the rotating suction drum 62, drawing the absorbent body material 61 into a depression-molding member 62*a* that is provided on the outer peripheral surface of the suction drum 62 and matches the shape of the absorbent body 4, and the absorbent body material 61 is laminated to form an absorbent body 4.

Next, the rotating suction drum 62 transfers and mounts the absorbent body 4 in the molding member 62*a* onto a carrier sheet 65 being conveyed in the machine direction MD under the suction drum 62. The carrier sheet 65 is conveyed downstream in the machine direction MD together with the mounted absorbent body 4, and is supplied to the following step.

The step of producing the absorbent body is followed by a step of forming a lamination body.

In this step, first the top sheet-forming apparatus 70 described below is used to form a continuous top sheet 71 with the top sheet 2 being continuous in the lengthwise direction. Also, the continuous top sheet 71 is laminated onto the first surface (onto the upper surface in FIG. 7) of the absorbent body 4 that is being conveyed in the machine direction MD and joined via an adhesive layer including a hot-melt adhesive, to produce a lamination body 72. The lamination body 72, once formed, is conveyed downstream in the machine direction MD and supplied to the following step.

The step of forming the lamination body is followed by a step of forming compressed grooves.

In this step, the lamination body 72 is passed between an upper roll 81 and a lower roll 82 in the embossing apparatus 80 to compress the continuous top sheet 71 and absorbent body 4 to form compressed grooves 41-43.

Here, the upper roll 81 of the embossing apparatus 80 includes protrusions (not shown) disposed on the outer peripheral surface and matching the positions and shapes of the compressed grooves 41-43, the protrusions compressing the lamination body 72 from the continuous top sheet 71 side in the thickness direction to form compressed grooves 41-43. The lower roll 82 is a roll having a flat outer peripheral surface, and it stably supports the lamination body 72 during compressing of the lamination body 72 by the upper roll 81.

In this step, a plurality of dotted compressed sections 44 are also to be formed. Therefore, the upper roll 81 includes protrusions for formation of the compressed sections 44, which are formed simultaneously with the compressed grooves 41-43. After formation of the compressed grooves 41-43 is complete, the lamination body 72 is conveyed downstream in the machine direction MD and supplied to the next step.

The step of forming the compressed grooves is followed by a step of forming a continuous sanitary napkin.

In this step, the continuous back sheet 91 that has been reeled out from the back sheet roll 90 is successively laminated onto the absorbent body 4 side surface of the lamination body 72 (onto the lower surface of the lamination body 72 in this case) via an adhesive layer including a hot-melt adhesive, to form a continuous sanitary napkin 92 in which a plurality of sanitary napkins 1 are directly connected in the lengthwise direction. As a result, the continuous top sheet 71 becomes joined to the first surface of the absorbent body 4 while the continuous back sheet 92 becomes bonded to the surface on the side opposite the first surface (the lower side of the absorbent body 4 in this case).

The continuous sanitary napkin 92 is conveyed downstream in the machine direction MD and supplied to the next step.

The step of forming the continuous sanitary napkin is followed by a cutting step.

In this step, the cutter of the cutting apparatus 100 is used to cut out individual sanitary napkins of the desired shapes and sizes from the continuous sanitary napkin.

This completes the sanitary napkin 1 as a product.

Incidentally, the step of forming the continuous top sheet, included in the step of forming the lamination body, is carried out in the following manner.

For the method of producing the continuous top sheet to serve as the top sheet 2, there are carried out, in order, a preheating step in which, from a top sheet roll 74 around which a long nonwoven fabric 73 to be processed serving as the starting material for the continuous top sheet 71 is wrapped as a roll, the nonwoven fabric 73 to be processed is unrolled, and the nonwoven fabric 73 to be processed that has been unrolled is preheated, and a shaping step in which the nonwoven fabric 73 to be processed that has passed through the preheating step is stretched and shaped.

Also, the method of producing the continuous top sheet is carried out using the top sheet-forming apparatus 70 as illustrated in FIG. 7 to FIG. 10. The forming apparatus 70 includes the aforementioned top sheet roll 74 that rolls out the nonwoven fabric 73 to be processed downstream in the machine direction MD, a preheating apparatus 76 that applies preheating to the nonwoven fabric 73 to be processed that has been formed by rolling out from the top sheet roll 74, and a shaping apparatus 77 that stretches the nonwoven fabric 73 to be processed that has been preheated, for shaping to form the raised sections 11 and furrow sections 12 (including the first recess sections 21 and second recess sections 26).

Incidentally, the continuous top sheet 71 formed in the step of forming a continuous top sheet as shown in FIG. 11 has basically the same structure as the top sheet 2, other than being long in the lengthwise direction, and therefore the same reference signs are used as for the top sheet 2, and will not be explained in detail.

In the preheating step, the long nonwoven fabric 73 to be processed, that has been rolled out from the top sheet roll 74 and conveyed along the machine direction MD, is successively contacted with the outer peripheral surfaces of a pair of rotating upper and lower heated rolls 76*a*, 76*b* of the preheating apparatus 76, to successively heat both sides of the nonwoven fabric 73 to be processed, thereby applying preheating. That is, the nonwoven fabric 73 to be processed that has been rolled out from the top sheet roll 74 is first taken up onto the outer peripheral surface of the lower heated roll 76*b* and one surface of the nonwoven fabric 73 to be processed in contact with the outer peripheral surface is heated. Next, the nonwoven fabric 73 to be processed is delivered so that the other surface opposite the surface heated by the lower heated roll 76*b* is contacted with the outer peripheral surface of the upper heated roll 76*a*, and the surface in contact with the outer peripheral surface is heated by the upper heated roll 76*a*.

The preheating temperature will depend on the type of thermoplastic resin fibers composing the nonwoven fabric to be processed, and for example, heating is preferably at above the temperature of initial melting of the thermoplastic resin fibers used in the nonwoven fabric to be processed, and a temperature below the melting point.

If the preheating temperature is at or above the melting point, the thermoplastic resin fibers will melt and harden, thus impairing the soft feel on the skin. Also if it is below the temperature of initial melting of the thermoplastic resin fibers, joining between the thermoplastic resin fibers will be maintained, making it difficult to shape the nonwoven fabric to be processed in the subsequent shaping step, and making it difficult to form suitable concavo-convexities.

For example, when the nonwoven fabric to be processed is made of core-sheath composite fibers including polyethylene terephthalate (PET) and high-density polyethylene (HDPE), the melting point temperature is 120° C. and the initial melting temperature is 50° C. or higher, and therefore the temperature of the outer peripheral surfaces of the heated roll is preferably about 50 to 110° C. and more preferably about 60 to 100° C.

In the shaping step, the nonwoven fabric 73 to be processed, that has passed through the preheating step and been conveyed, is inserted between the interlocking and rotating pair of upper and lower stretching rolls 78, 79 of the shaping apparatus 77, stretching the nonwoven fabric 73 to be processed between the ridges 78a and grooves 78b of the upper stretching roll 78 and the recesses 79b and pins 79a of the lower stretching roll 79 which are interlocking, to shape it.

To facilitate shaping when carrying out the shaping step, it is preferably carried out while heating the stretching rolls 78, 79. The heating temperature during this time is preferably higher than the preheating temperature during the preheating step, and a lower temperature than the melting point of the nonwoven fabric 73 to be processed.

Figure 8:
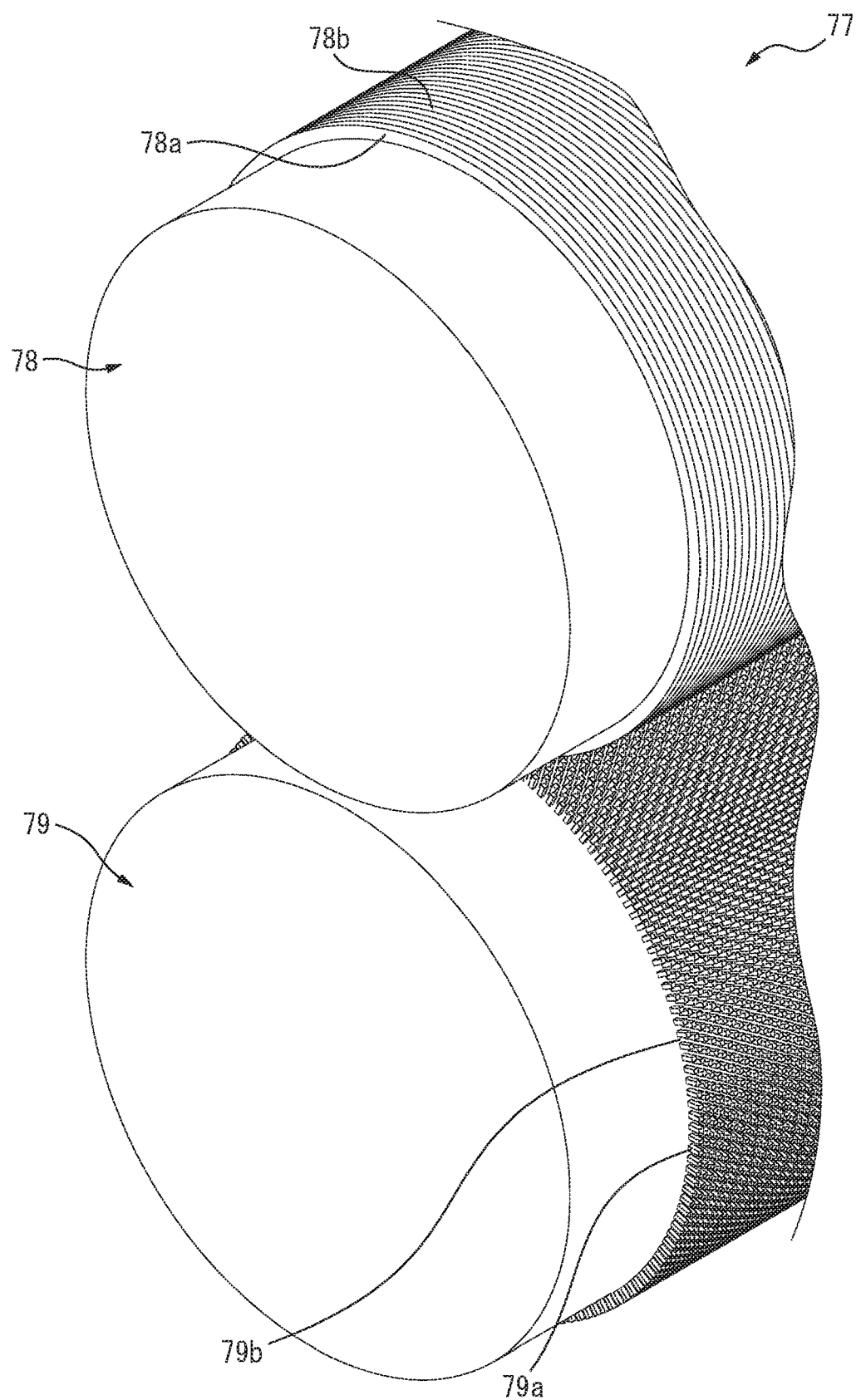
FIG. 8 is a perspective view schematically showing stretching rolls of a shaping apparatus of FIG. 7.

Specifically, as shown in FIG. 8, the upper stretching roll 78 includes, on the outer peripheral surface at fixed intervals in the widthwise direction of the roll, the aforementioned rows of ridges 78a formed in mutually parallel along the outer peripheral surface of the upper stretching roll 78, and the aforementioned rows of grooves 78b formed between adjacent ridges 78a, 78a.

Figure 9:
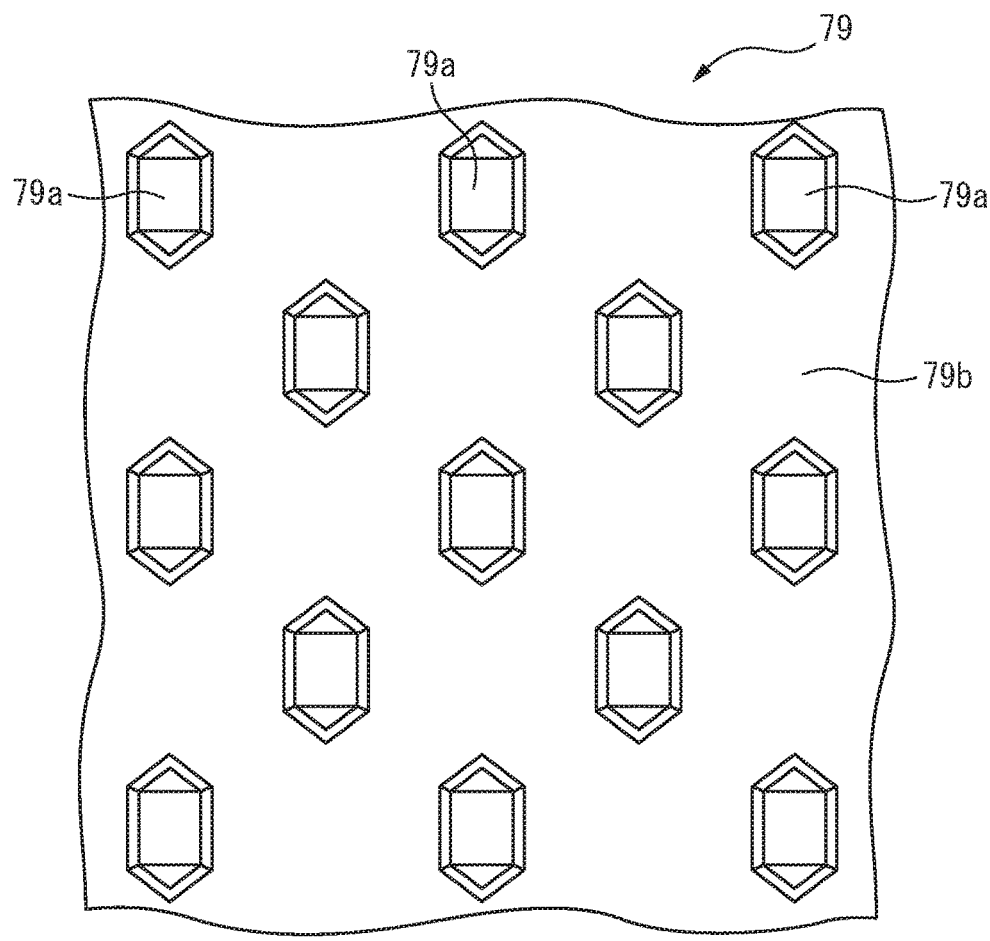
FIG. 9 is a schematic view showing an arrangement of pins in a lower shaping roll.

Also, the lower stretching roll 79 includes, on its outer peripheral surface, a plurality of pins 79a provided so as to interlock with the grooves 78b of the upper stretching roll 78, and recesses 79b that interlock with its ridges 78a. As shown in FIG. 8, the pins 79a are disposed at a constant interval in the widthwise direction of the roll so as not to contact the ridges 78a of the upper stretching roll 78 (the interval by which the portions where the pins 79a are not present across the full width of the lower stretching roll 79 in this embodiment), while being linearly disposed at approximately constant interval along the outer peripheral surface, with respect to the circumferential direction of the roll. Also, as shown in FIG. 9, the lower stretching roll 79 of this embodiment has a structure in which a plurality of pins 79a are disposed in a zigzag fashion around the outer peripheral surface of the lower stretching roll 79.

Figure 10:
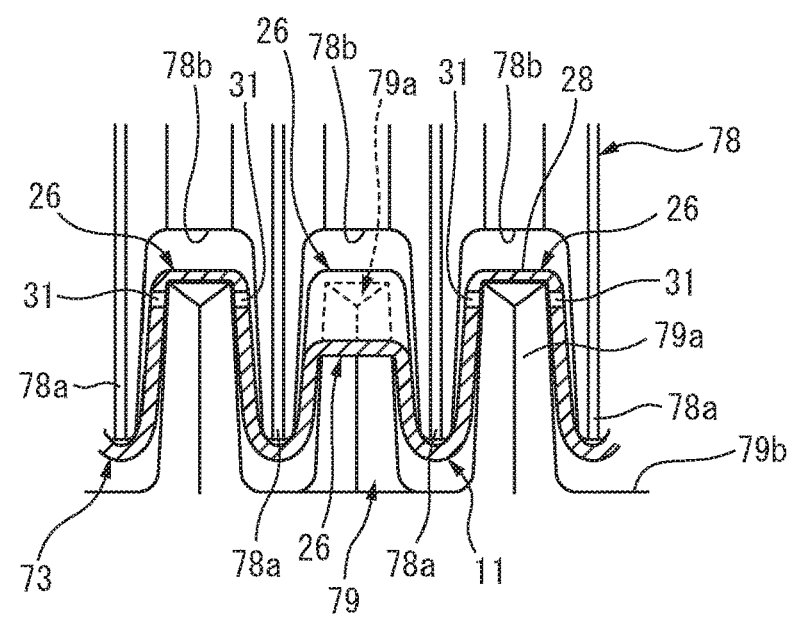
FIG. 10 is a partial magnified view schematically showing an interlocked state of an upper shaping roll and lower shaping roll.

When carrying out the shaping step, as shown in FIG. 10, the upper stretching roll 78 pushes the portions where the ridges 78a contact with the nonwoven fabric 73 to be processed, into the recesses 79b of the lower stretching roll 79, thereby shaping the raised sections 11 of the top sheet 2 (which is the continuous top sheet 71 at this stage).

Meanwhile, the lower stretching roll 79 forces its plurality of pins 79a aligned in rows in the circumferential direction, into the nonwoven fabric 73 to be processed contacting at the tip sections of the pins 79a, at the corresponding grooves 78b of the upper stretching roll 78. During this time, the portions of the nonwoven fabric 73 to be processed that have been pulled into the grooves 78b without being in contact with the pins 79a are minimally stretched compared to the other portions, and become the first bottom sections 22 of the first recess sections 21 of the furrow sections 12 of the top sheet 2 (continuous top sheet 71). Also, the portions that were in contact with the tip sections of the pins 79a are strongly forced into the grooves 78b and shaped, thereby forming second recess sections 26 of the top sheet 2 (continuous top sheet 71) including perimeter wall sections 27 and second bottom sections 28.

During formation, the tip sections of the pins 79a push the contacting portions of the nonwoven fabric 73 to be processed into the grooves 78b while the upper stretching roll 78 and lower stretching roll 79 are meshed with the nonwoven fabric 73 to be processed at the second bottom sections 28 of the second recess sections 26, and therefore the fiber density is essentially higher than at the other portions and the rigidity is increased. Thus, the top sheet 2 (continuous top sheet 71) results in improved rigidity for the nonwoven fabric 73 as a whole section, by the action of the bottom sections 28 of the recess sections 26. Also, since portions are present where no pins 79a are present across the entire roll width of the lower stretching roll 79, portions are formed in the continuous top sheet 71 where no second recess sections 26 are formed across the entire width (see top sheet 2 in FIG. 5).

Furthermore, at the portions of the nonwoven fabric 73 to be processed that were in contact with both edges of the tip sections of the pins 79a in the widthwise direction (widthwise direction of the roll), with the help of the tension produced when the ridges 78a of the upper stretching roll 78 push the nonwoven fabric 73 to be processed into the recesses 79b of the lower stretching roll 79, the pins 79a shove aside the thermoplastic resin fibers forming the first perimeter wall sections 29 among the perimeter wall sections of the second recess sections, or they break the fibers to form the aforementioned broken fibers with broken ends.

This results in formation of the hole sections 31 having perimeter sections that include broken ends of broken fibers, in the second recess sections 26. Incidentally, some of the thermoplastic resin fibers remain in a state spanning across the interior spaces of the hole sections 31, with some of the broken ends of the broken fibers extending into the interior spaces of the hole sections 31.

Since the hole sections 31 are formed in the direction of the nonwoven fabric 73 to be processed that is along the machine direction MD, i.e. the rotational direction of the stretching rolls 78, 79, which is the direction in which the raised sections 11 and the furrow sections 12 are extended, the hole sections 31 are also formed on the first perimeter wall sections 29 which are the peripheral surfaces, along the direction in which the raised sections 11 and the furrow sections 12 are extended.

When the shaping step is complete, this completes the continuous top sheet 71 shown in FIG. 11, and the continuous top sheet 71 is then conveyed toward the absorbent body 4 on the carrier sheet 65, for lamination onto the absorbent body 4, and is laminated and joined on the upper side of the absorbent body 4 via an adhesive layer. During this time, in the continuous top sheet 71, at least some of the second surfaces 2b of the first bottom sections 22 of the first recess sections 21, and the second surfaces 2b of the second bottom sections 28 of the second recess sections 26, are joined with the upper surface of the absorbent body 4, while essentially none of the second surfaces 2b of the raised sections 11 are joined.

Each of the steps described above are then carried out to complete the sanitary napkin 1 as a product.

With the top sheet 2 in the sanitary napkin 1 having this structure, the raised sections 11 that are not joined to the absorbent body 4 can move freely, and the softness upon contacting the skin is not impaired.

On the other hand, since the second recess sections 26 of the furrow sections 12 are joined to the absorbent body at the second bottom sections 28 that have the highest fiber density in the top sheet 2, it is possible to stably join the top sheet 2 to the absorbent body 4, to stably reduce detachment of the top sheet 2 from the absorbent body 4, and to minimize impairment of the fluid absorption property.

As a result, it is possible to ensure both excellent feel on the skin and high liquid absorption.

According to this embodiment, portions of the first bottom sections 22 are joined to the top sheet side portion of the absorbent body 4, but the first bottom sections do not necessarily need to be joined to the absorbent body 4 so long as the top sheet and the absorbent body are stably joined. In this case as well, the second bottom sections must be reliably joined to the top sheet side of the absorbent body.

For the embodiment described above, the distance between the portions of the second surfaces 2b at the top sections 13 of the raised sections 11 and the top sheet side portion of the absorbent body 4 is smaller than the distance between the portions of the first surfaces 2a of the first bottom sections 22 nearest the absorbent body 4 and the top sheet side portion of the absorbent body 4.

However, so long as detachment between the top sheet and absorbent body can be stably reduced, the relationship between the distance between the portions of the second surfaces 2b at the top sections of the raised sections and the top sheet side portions of the absorbent body, and the distance between the portions of the first surfaces of the first bottom sections nearest the absorbent body and the top sheet side portions of the absorbent body, does not necessarily need to be such a relationship.

For the embodiment described above, the top sheet 2 has a structure in which at least two raised sections 11 are situated between a second recess section 26 and other second recess section 26 adjacent to that second recess section 26 in the widthwise direction. However, the number of raised sections between the second recess sections may be set as desired.

For the embodiment described above, in the top sheet 2, the structure in which a first recess section 21 of a furrow section 12 and a first recess section 21 of other furrow section adjacent to that furrow section 12 are mutually adjacent is a structure having a portion that is continuous over the entire width in the widthwise direction. However, the top sheet does not necessarily need to have such a structure.

In the embodiment described above, the perimeter wall section 27 has a pair of first perimeter wall sections 29, 29 formed along the lengthwise direction, and a pair of second perimeter wall sections 30, 30 formed along the widthwise direction, and hole sections 31 passing through to the second surface 2b are formed in the pair of first perimeter wall sections 29, 29.

However, so long as the softness of the raised sections can be ensured, there is no need to use hole sections in the perimeter wall sections.

According to the embodiment described above, the second surfaces of the second bottom sections are formed flat, but so long as it is possible to adequately ensure the softness of the second surfaces of the second bottom sections, the second surfaces do not necessarily need to be flat. Moreover, the absorbent article (sanitary napkin 1) of the embodiment described above includes, on the top sheet side surface, compressed sections 44 extending in the widthwise direction where the top sheet 2 and absorbent body 4 have been compressed in the thickness direction, but such compressed sections do not necessarily need to be provided.

In addition, this embodiment was described assuming a sanitary napkin as the absorbent article, but the absorbent article may be any type of absorbent article such as a disposable diaper, incontinence pad (panty liner) or the like.

REFERENCE SIGNS LIST

1 Sanitary napkin (absorbent article)
2 Top sheet
3 Back sheet
4 Absorbent body
11 Raised section
12 Furrow section
13 Top section
21 First recess section
22 First bottom section
26 Second recess section
27 Perimeter wall section
28 Second bottom section
29 First perimeter wall section
30 Second perimeter wall section
31 Hole section
41-43 Compressed grooves

The invention claimed is:

1. An absorbent article having a lengthwise direction, a widthwise direction and a thickness direction and comprising:
   a liquid-permeable top sheet;
   a liquid-impermeable back sheet; and
   an absorbent body disposed between the top sheet and the back sheet,
   wherein
   the top sheet has a first surface located on an opposite side from the absorbent body and a second surface on the absorbent body side, and comprises:
      a plurality of raised sections protruding in a direction toward the first surface, which are extended in the lengthwise direction and formed at predetermined intervals in the widthwise direction, and
      a plurality of furrow sections depressed in a direction toward the second surface, which are extended in the lengthwise direction and formed between the raised sections,
   each of the furrow sections comprises
      a first single recess section including a first bottom section located further in a direction toward the absorbent body than a location of the first surface at a top section of each of the raised sections, and
      a plurality of second recess sections formed discontinuously in the lengthwise direction inside the first single recess section and formed as depressions opening into the first bottom section,
   each of the second recess sections comprises
      a perimeter wall section extending from the first bottom section in a direction toward the absorbent body, and
      a second bottom section formed on an edge of the perimeter wall section on the absorbent body side so as to plug the edge and having a highest fiber density in the top sheet, and
   in the each raised section, at least a portion of the second surface at the top section is not joined to the absorbent body, and in at least the each second recess section of the each furrow section, the second bottom section is joined to the absorbent body.

2. The absorbent article according to claim 1, wherein at least a portion of the first bottom section is joined with a top sheet side portion of the absorbent body.

3. The absorbent article according to claim 2, wherein a distance between the portion of the second surface at the top section of the raised section and the top sheet side portion of the absorbent body is smaller than a distance between a portion of the first bottom section at the first surface that are nearest the absorbent body and the top sheet side portion of the absorbent body.

4. The absorbent article according to claim 1, wherein the top sheet has a structure with at least two raised sections situated between one of the second recess sections and another of the second recess sections adjacent to the one second recess section in the widthwise direction.

5. The absorbent article according to claim 1, wherein, in a portion of the top sheet a structure, in which the first single recess section of one of the furrow sections and the first single recess sections of other furrow sections adjacent to the one furrow section are mutually adjacent, is continued over an entire width of the portion of the top sheet in the widthwise direction.

6. The absorbent article according to claim 1, wherein the perimeter wall section has a pair of first perimeter wall sections formed along the lengthwise direction, and a pair of second perimeter wall sections formed along the widthwise direction, and includes hole sections passing through to the second surface in the pair of first perimeter wall sections.

7. The absorbent article according to claim 1, wherein the second surface of the second bottom section is flat.

8. The absorbent article according to claim 1, wherein the top sheet has a structure in which a region of the first surface and a region of the second surface of the raised section are curved into shapes so as to be convex in a direction from the second surface toward the first surface, while a region of the first surface and a region of the second surface in the first single recess section of each of the furrow sections are curved into shapes so as to be convex in a direction from the first surface toward the second surface.

9. The absorbent article according to claim 1, further comprising, on a top sheet side surface of the absorbent body, a compressed groove extending in the widthwise direction, wherein the top sheet and the absorbent body have been compressed in the thickness direction.

10. The absorbent article according to claim 1, wherein, in each of the furrow sections, the second recess sections are further depressed from the first single recess section to form the depressions.

11. An absorbent article having a lengthwise direction, a widthwise direction and a thickness direction and comprising:
a liquid-permeable top sheet;
a liquid-impermeable back sheet; and
an absorbent body disposed between the top sheet and the back sheet,
wherein
the top sheet has a first surface located on an opposite side from the absorbent body and a second surface on the absorbent body side, and comprises:
a plurality of raised sections protruding in a direction toward the first surface, which are extended in the lengthwise direction and formed at predetermined intervals in the widthwise direction, and
a plurality of furrow sections depressed in a direction toward the second surface, which are extended in the lengthwise direction and formed between the raised sections,
each of the furrow sections comprises
a first recess section including a first bottom section located further in a direction toward the absorbent body than a location of the first surface at a top section of each of the raised sections, and
a plurality of second recess sections formed discontinuously in the lengthwise direction inside the first recess section and further depressed from the first recess section to form depressions opening into the first bottom section,
each of the second recess sections comprises a perimeter wall section extending from the first bottom section in a direction toward the absorbent body, and a second bottom section formed on an edge of the perimeter wall section on the absorbent body side so as to plug the edge and having a highest fiber density in the top sheet, and
in the each raised section, at least a portion of the second surface at the top section is not joined to the absorbent body, and in at least the each second recess section of the each furrow section, the second bottom section is joined to the absorbent body.

12. An absorbent article having a lengthwise direction, a widthwise direction and a thickness direction and comprising:
a liquid-permeable top sheet;
a liquid-impermeable back sheet; and
an absorbent body disposed between the top sheet and the back sheet,
wherein
the top sheet has a first surface located on an opposite side from the absorbent body and a second surface on the absorbent body side, and comprises:
a plurality of raised sections protruding in a direction toward the first surface, which are extended in the lengthwise direction and formed at predetermined intervals in the widthwise direction, and
a plurality of furrow sections depressed in a direction toward the second surface, which are extended in the lengthwise direction and formed between the raised sections,
each of the furrow sections comprises
a first recess section including a first bottom section located further in a direction toward the absorbent body than a location of the first surface at a top section of each of the raised sections, and
a plurality of second recess sections formed discontinuously in the lengthwise direction inside the first recess section and formed as depressions opening into the first bottom section,
each of the second recess sections comprises
a perimeter wall section extending from the first bottom section in a direction toward the absorbent body, and
a second bottom section formed on an edge of the perimeter wall section on the absorbent body side so as to plug the edge and having a highest fiber density in the top sheet,
in the each raised section, at least a portion of the second surface at the top section is not joined to the absorbent body, and in at least the each second recess section of the each furrow section, the second bottom section is joined to the absorbent body,
at least a portion of the first bottom section is joined with a top sheet side portion of the absorbent body, and
a distance between the portion of the second surface at the top section of the raised section and the top sheet side portion of the absorbent body is smaller than a distance between a portion of the first bottom section at the first surface that are nearest the absorbent body and the top sheet side portion of the absorbent body.

13. An absorbent article having a lengthwise direction, a widthwise direction and a thickness direction and comprising:
- a liquid-permeable top sheet;
- a liquid-impermeable back sheet; and
- an absorbent body disposed between the top sheet and the back sheet, wherein the top sheet has a first surface located on an opposite side from the absorbent body and a second surface on the absorbent body side, and comprises:
- a plurality of raised sections protruding in a direction toward the first surface, which are extended in the lengthwise direction and formed at predetermined intervals in the widthwise direction, and
- a plurality of furrow sections depressed in a direction toward the second surface, which are extended in the lengthwise direction and formed between the raised sections, each of the furrow sections comprises
- a first recess section including a first bottom section located further in a direction toward the absorbent body than a location of the first surface at a top section of each of the raised sections, and
- a plurality of second recess sections formed discontinuously in the lengthwise direction inside the first recess section and formed as depressions opening into the first bottom section, each of the second recess sections comprises
- a perimeter wall section extending from the first bottom section in a direction toward the absorbent body, and
- a second bottom section formed on an edge of the perimeter wall section on the absorbent body side so as to plug the edge and having a highest fiber density in the top sheet, in the each raised section, at least a portion of the second surface at the top section is not joined to the absorbent body, and in at least the each second recess section of the each furrow section, the second bottom section is joined to the absorbent body, and the perimeter wall section has a pair of first perimeter wall sections formed along the lengthwise direction, and a pair of second perimeter wall sections formed along the widthwise direction, and includes hole sections passing through to the second surface in the pair of first perimeter wall sections.

* * * * *